(12) United States Patent
Martiniuk et al.

(10) Patent No.: US 11,839,641 B2
(45) Date of Patent: Dec. 12, 2023

(54) METHODS AND COMPOSITIONS FOR TREATMENT OF LYSOSOMAL STORAGE DISORDERS

(71) Applicant: JME Group Associates Inc., Roseland, NJ (US)

(72) Inventors: Frank Martiniuk, Wood Ridge, NJ (US); Elena Arvanitopoulos, Roseland, NJ (US); John Arvanitopoulos, Roseland, NJ (US); Angelo Kambitsis, Staten Island, NY (US)

(73) Assignee: JME GROUP ASSOCIATES INC., Roseland, NJ (US)

( * ) Notice: Subject to any disclaimer, the term of this patent is extended or adjusted under 35 U.S.C. 154(b) by 80 days.

(21) Appl. No.: 17/404,680

(22) Filed: Aug. 17, 2021

(65) Prior Publication Data

US 2022/0054579 A1     Feb. 24, 2022

Related U.S. Application Data

(60) Provisional application No. 63/067,483, filed on Aug. 19, 2020.

(51) Int. Cl.
*A61K 36/8998*     (2006.01)
*A61P 43/00*     (2006.01)
*A61K 38/46*     (2006.01)

(52) U.S. Cl.
CPC .......... *A61K 36/8998* (2013.01); *A61K 38/46* (2013.01); *A61P 43/00* (2018.01)

(58) Field of Classification Search
None
See application file for complete search history.

(56) References Cited

PUBLICATIONS

Chien et al (Pediatrics and Neonatology 54:219-227, 2013) (Year: 2013).*
Hubner et al (Eur Food Res Technol 231:27-35, 2010) (Year: 2010).*
Rico et al (Foods 9:19 pages, 2020) (Year: 2020).*
Zhou et al (Food Sci Biotechnol 22:1753-1761, 2013) (Year: 2013).*
Deng et al (Int J Molecular Sciences 21:20 pages, 2020) (Year: 2020).*
Malunga et al (Frontiers in Nutrition, 8:9 pages, 2021) (Year: 2021).*
Frandsen et al., "Purification, Enzymatic Characterization, and Nucleotide Sequence of a High-Isoelectric-Point from Barley Malt," Plant Physiology 123:275-286 (2000).
Raben et al., "Enzyme Replacement Therapy in the Mouse Model of Pompe Disease," Mol Genet Metab. 80:159-169 (2003).
Martiniuk et al., "Further Studies of the Structure of Human Placental Acid Alpha-Glucosidase," Arch Biochem Biophys 231:454-460 (1984).
Andriotis et al., "The Maltase Involved in Starch Metabolism in Barley Endosperm is Encoded by a Single Gene," PLoS ONE 11:e0151642 (2016).
Van Gelder et al., "Enzyme Therapy and Immune Response in Relation to CRIM Status: The Dutch Experience in Classic Infantile Pompe Disease," J Inherit Metab Dis.38:305-314 (2015).
Martiniuk et al., "Correction of Glycogen Storage Disease Type II by Enzyme Replacement With a Recombinant Human Acid Maltase Produced by Over-Expression in a CHO-DHFR (Neg) Cell Line," Biochem Biophys Res Commun. 276:917-923 (2000).
Raben et al., "Targeted Disruption of the Acid Alpha-Glucosidase Gene in Mice Causes an Illness with Critical Features of Both Infantile and Adult Human Glycogen Storage Disease Type II," J Biol Chem. 273:19086-19092 (1998).
Jung et al., "Production and Characterization of Recombinant Human Acid Alpha-Glucosidase in Transgenic Rice Cell Suspension Culture", J. Biotechnology 226:44-53 (2016).
Jung et al., "Production of Recombinant Human Acid α-Glucosidase With High-Mannose Glycans in gnt1 Rice for the Treatment of Pompe Disease", J. Biotechnology 249:42-50 (2017).
Martiniuk et al., "Production of a Functional Human Acid Maltase in Tobacco Seeds: Biochemical Analysis, Uptake by Human GSDII Cells, and in vivo Studies in GAA Knockout Mice," Appl Biochem Biotechnol. 171:916-926 (2013).

* cited by examiner

*Primary Examiner* — Craig D Ricci
(74) *Attorney, Agent, or Firm* — Troutman Pepper Hamilton Sanders LLP (Rochester)

(57) ABSTRACT

This application relates to the treatment of lysosomal storage disorders resulting from a deficiency of acid maltase and/or acid α-glucosidase by administering active barley in comminuted form. Also disclosed are methods of replacing acid maltase and/or acid α-glucosidase by administering active barley in comminuted form. Further disclosed are compositions for carrying out these methods.

11 Claims, 9 Drawing Sheets

METHODS AND COMPOSITIONS FOR TREATMENT OF LYSOSOMAL STORAGE DISORDERS

This application claims the priority benefit of U.S. Provisional Patent Application Ser. No. 63/067,483, filed Aug. 19, 2020, which is hereby incorporated by reference in its entirety.

FIELD

The present application relates to methods and compositions for treating lysosomal storage disorders.

BACKGROUND

Genetic deficiency of lysosomal acid maltase or acid α-glucosidase ("GAA") results in the orphan disease known as glycogen storage disease type II ("GSDII") or acid maltase deficiency ("AMD") or Pompe's disease ("PD"), encompassing at least five clinical subtypes of varying severity. These diseases are classified as glycogen storage diseases and are a type of lysosomal storage diseases. GSDII, AMD, and PD result from mutations in the GAA gene and deficient GAA activity, leading to the accumulation of glycogen in tissues (primarily muscle) and characterized by progressive skeletal muscle weakness and respiratory insufficiency. Lysosomal glycogen accumulation leads to multiple secondary abnormalities (autophagy, lipofuscin, mitochondria, trafficking and signaling) that may be amenable to long-term therapy (Douillard-Guilloux et al., "Restoration of Muscle Functionality by Genetic Suppression of Glycogen Synthesis in a Murine Model of Pompe Disease," *Human Molecular Genetics* 19:684-696 (2010)).

The incidence of glycogen storage disease is about 1/40,000 births (Martiniuk et al., "Carrier Frequency for Glycogen Storage Disease Type II in New York and Estimates of Affected Individuals Born with the Disease," *Am J Med Genet.* 79:69-72 (1998)), and it is estimated that there are approximately 4,000 accumulated cases in the USA and approximately 100,000 cases worldwide. Currently, there is no cure for glycogen storage disease type II, acid maltase deficiency, or Pompe's disease.

The current approved enzyme replacement therapy ("ERT") for GSDII, AMD, and PD is via intravenous infusion of a recombinant human GAA ("rhGAA") produced by CHO cells (MYOZYME® (alglucosidase alfa), Sanofi Genzyme) once every 2 weeks, which has shown varying efficacy in patients. Although the current ERT has proven to be very efficient in rescuing cardiac abnormalities and extending the life span of infants, the response in skeletal muscle is variable. In late-onset patients, only mild improvements in motor and respiratory functions have been achieved and the current ERT is unsatisfactory in the reversal of skeletal muscle pathology.

Additional challenges for ERT include insufficient targeting/uptake of enzyme into disease-relevant tissues and poor tolerability due to severe ERT-mediated anaphylactic and immunologic reactions. Lifelong ERT can be prohibitively expensive ($250-500 k/adult patient/year) resulting in the reluctance of insurance companies to reimburse costs for late-onset patients (Hundsberger et al., "Swiss National Guideline for Reimbursement of Enzyme Replacement Therapy in Late-onset Pompe Disease," *J Neurol.* 260:2279-85 (2013)), thus underlining the demand for more economical production and novel delivery strategies. Hence, novel approaches for ERT for GSDII, AMD, and PD treatment are urgently needed.

The present application is directed to overcoming these and other deficiencies in the art.

SUMMARY

One aspect of the present application is directed to a method of treating a lysosomal storage disease resulting from a deficiency of acid maltase and/or acid α-glucosidase. This method involves selecting a subject having lysosomal storage disease resulting from a deficiency of acid maltase and/or acid α-glucosidase and administering active barley in comminuted form to the selected subject to treat the lysosomal storage disease.

Another aspect of the present application is directed to a method of replacing acid maltase and/or acid α-glucosidase in a subject. This method involves selecting a subject in need of replacing acid maltase and/or acid α-glucosidase and administering active barley in comminuted form to the selected subject to replace acid maltase and/or acid α-glucosidase in the selected subject.

Yet another aspect of the present application is directed to a therapeutic composition comprising active germinated barley in comminuted form and an edible pharmaceutically acceptable carrier.

A further aspect of the present application is directed to a therapeutic system comprising active germinated barley in comminuted form and an enzyme replacement therapeutic.

As described herein, the development of active barley provides a unique source for therapeutic oral enzyme replacement therapy that can be administered for treatment of glycogen storage diseases such as GSDII, AMD and PD alone and as a supplement to alglucosidase alfa treatment. Active barley provided enzymatically active bGAA that reversed the AMD clinical phenotype presentation in a dose-dependent manner in GAA KO mice, a model for glycogen storage disease. Despite the low sequence similarity of bGAA compared to the human GAA enzyme, the barley GAA enzyme was shown to be taken up by both human and murine white blood cells in a similar fashion as human recombinant GAA. Furthermore, the oral delivery of barley GAA was surprisingly shown to be efficacious in improving multiple indices of skeletal muscle and cognitive neurological function that were affected by the lysosomal storage disorder caused by GAA deficiency. Major advantages of ground germinated barley ("GGB") include its extreme stability at room temperature (not requiring refrigeration), low cost compared to current treatments, ease of administration (not requiring a visit to a physician's office or clinic, or intravenous infusion), reduced or absent immunological reaction, and ability to reverse neurological problems.

DETAILED DESCRIPTION

A first aspect of the present application is directed to a method of treating a lysosomal storage disease resulting from a deficiency of acid maltase and/or acid α-glucosidase. This method involves selecting a subject having lysosomal storage disease resulting from a deficiency of acid maltase and/or acid α-glucosidase and administering active barley in comminuted form to the selected subject to treat the lysosomal storage disease.

In accordance with this and all aspects of the present application, the term "subject" or "patient" refers to a mammal, preferably a human with a lysosomal storage disease. The terms "treatment" or "treating", as used herein, refer to therapy, particularly refers to the administration of medicine or performing medical procedures with respect to a patient, to cure or reduce the extent of the infirmity or malady or condition or event, or to slow down an undesired physiological condition, disorder or disease, or to obtain beneficial or desired clinical results such as partial or total restoration or inhibition in decline of a parameter, value, function or result that had or would become abnormal.

For the purposes of this application, beneficial or desired clinical results include, but are not limited to, alleviation of symptoms; diminishment of the extent or vigor or rate of development of the condition, disorder or disease; stabilization (that is, not worsening) of the state of the condition, disorder or disease; slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects. In the present application, the treatments using the compositions and methods described may be provided to treat a glycogen storage disease. Most preferably, treatment is for the purpose of reducing or diminishing the symptoms or progression of a disease or disorder of glycogen storage. Treating as used herein also means that the compositions of the present application may be administered to a subject already suffering from the disease.

As used herein, the terms "administer," "administering" or "administration" refer to directly administering a compound or a composition to a subject. Administering a composition may be accomplished by injection, topically, orally, or by any of these methods in combination with other known techniques.

The term "disease" as used herein is intended to be generally synonymous, and is used interchangeably with, the terms "disorder," "dysfunction," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

There are several types of lysosomal storage diseases resulting from deficiency of acid maltase and/or acid α-glucosidase caused by mutations in the GAA gene called "glycogen storage disease type II", "GSDII", "acid maltase deficiency", "AMD", "Pompe's disease", and "PD", all of which can be treated in accordance with the various methods and compositions as described herein. These lysosomal storage diseases can vary in onset from early (infantile) to late (juvenile or adult) forms. The infantile form (historically known as Pompe's disease and also known as infantile glycogen storage disease type II), exhibits no GAA enzyme activity, muscle weakness, feeding difficulties, hypertrophic cardiomyopathy, and leads to death in the first year (Tagers et al., "Alpha Glucosidase Deficiency; Pompe's Disease," *Enzyme* 38:280-285 (1987); van den Hout, "The Natural Course of Infantile Pompe's Disease: 20 Original Cases Compared with 133 Cases from the Literature," *Pediatrics* 112:332-340 (2003); Winkel et al., "The Natural Course of Non-Classic Pompe's Disease; a Review of 225 Published Cases," *J Neurol.* 252:875-884 (2005), each of which is hereby incorporated by reference in their entirety).

The late-onset form has partial GAA enzyme deficiency with slowly progressive muscle weakness leading to wheelchair/ventilator dependence and death from respiratory insufficiency (Engel et al., "The Spectrum and Diagnosis of Acid Maltase Deficiency," *Neurology* 23:95-106 (1973); Mehler and DiMauro, "Residual GAA Activity in Late-Onset Acid Maltase Deficiency," *Neurol.* 27:178-184 (1997); Slonim et al., "Identification of Two Subtypes of Infantile Acid Maltase Deficiency: Evaluation of Twenty-Two Patients and Review of the Literature," *J Pediatrics* 137:283-285 (2000); La Badie, "Biochemical and Immunologic Studies of Acid Alpha Glucosidase Deficiency, a Genetically Heterogeneous, Inherited Neuromuscular Disease," Ph.D. Thesis, City University of New York, Mt. Sinai Hospital (1986), each of which is hereby incorporated by reference in their entirety).

In accordance with this and other aspects of the present application, the lysosomal storage disease is selected from the group consisting of glycogen storage disease type II, acid maltase deficiency, Pompe's disease, and combinations thereof. In some embodiments, the glycogen storage disease type II is selected from the group consisting of infantile glycogen storage disease type II, juvenile glycogen storage disease type II, or adult-onset glycogen storage disease type II.

It is also contemplated that the compositions and methods of the present application described herein can be used to treat a lysosomal storage disease in conjunction with another pharmaceutical agent. The compositions of the present application can be used, alone or in combination with other pharmaceutically active compounds, to treat conditions such as those described above. The compositions of the present application and other pharmaceutically active compositions can be administered simultaneously (either in the same dosage form or in separate dosage forms) or sequentially.

As used herein, the terms "acid maltase", "lysosomal acid maltase", "acid α-glucosidase" and "GAA" mean proteins with acid α-glucosidase activity. The terms "recombinant human acid α-glucosidase", "rhGAA", and "alglucosidase alfa" are used interchangeably and mean human GAA. Formulations with alglucosidase alfa derived from CHO cells include MYOZYME® (Sanofi Genzyme) and LUMIZYME® (Sanofi Genzyme).

As used herein, enzyme replacement therapy ("ERT") refers to the exogenous administration of GAA to provide GAA enzyme that is deficient in patients with glycogen storage disease. Accordingly, in this and other aspects of the methods described herein, the method may be carried out in conjunction with enzyme replacement therapy. Alglucosidase alfa (MYOZYME®) is a pharmaceutical agent administered as a form of enzyme replacement therapy. In some embodiments, the method is carried out in conjunction with alglucosidase alfa treatment. In some embodiments, the alglucosidase alfa is administered intravenously. In some embodiments, the alglucosidase alfa is administered intravenously at 20 mg/kg every 2 weeks. In some embodiments, the alglucosidase alfa is administered intravenously at 50 mg/kg weekly.

In accordance with the compositions and methods of the present application described herein, the terms "active barley" or "enzymatically active barley", or "active germinated barley" mean barley that has barley GAA ("bGAA") enzymatic activity. The term "GGB" means ground germinated barley, which is active barley that has been comminuted.

Barley GAA is a high-isoelectric-point (pI) α-glucosidase (Frandsen et al., "Purification, Enzymatic Characterization, and Nucleotide Sequence of a High-Isoelectric-Point α-Glucosidase from Barley Malt," *Plant Physiology* 123:275-286 (2000), which is hereby incorporated by reference in its entirety). The enzyme has high activity toward maltose (kcat=25 s$^{-1}$), with an optimum activity at pH 4.5. Acarbose (an α-glucosidase inhibitor) was a strong inhibitor of this enzyme (Ki=1.5 μM).

Gene expression analysis of barley GAA showed that transcription reached a maximum 48 h after the start of germination (Frandsen et al., "Purification, Enzymatic Characterization, and Nucleotide Sequence of a High-Isoelectric-Point α-Glucosidase from Barley Malt," *Plant Physiology* 123:275-286 (2000), which is hereby incorporated by reference in its entirety). There are two bGAAs with high and low pI's. These two bGAA isoforms may be encoded by only one gene due to proteolysis and post-translational modifications (Andriotis et al., "The Maltase Involved in Starch Metabolism In Barley Endosperm is Encoded By a Single Gene," *PLoS ONE* 11:e0151642 (2016), which is hereby incorporated by reference in its entirety).

According to this and other aspects of methods and compositions described herein, the active barley is in germinated form. Suitable barley germination times include, without limitation, germination for less than 1 day, germination for at least 1 day, germination for at least 2 days, germination for at least 3 days, germination for at least 4 days, germination for at least 5 days, germination for at least 6 days, germination for at least 7 days, germination for at least 8 days, germination for at least 9 days, germination for at least 10 days, germination for more than 10 days. In a preferred embodiment, the barley is germinated for 7-8 days. In some embodiments, the barley is tested for GAA activity and germinated until GAA activity is at a peak level for that barley variety.

In some embodiments of the methods and compositions described herein, active barley is produced by treating barley seeds with gibberellic acid to induce germination. Gibberellic acid (GA) is a simple gibberellin, promoting growth and elongation of cells. GA stimulates the cells of germinating seeds to produce mRNA molecules that code for hydrolytic enzymes. GA is usually used in concentrations between 0.01 and 10 mg/liter (Hardy, "General Aspects and Applications of Gibberellins and Gibberellic Acid in Plants," In: Hardy, J., Gibberellins and Gibberellic Acid: Biosynthesis, Regulation and Physiological Effects. ed. Hauppauge: *Nova Science Publishers* 1-21 (2015), which is hereby incorporated by reference in its entirety). Soaking seeds in GA for 24-36 hours is a rapid and efficient treatment to break dormancy of seeds (Rodrigues Vieira et al., "Action of Gibberellic Acid (GA3) on Dormancy and Activity of α-Amylase in Rice Seeds," *Revista Brasileira de Sementes* 24:43-48 (2002); (Briggs, "Biochemistry of Barley Germination Action Of Gibberellic Acid On Barley Endosperm," *Brewing Ind Res Found* 69:244-248 (1963), each of which is hereby incorporated by reference in their entirety). In some embodiments, without limitation, the active barley is processed after 1 day of germination, after 2 days of germination, after 3 days of germination, after 4 days of germination after 5 days of germination, after 6 days of germination, after 7 days of germination, after 8 days of germination, after 9 days of germination, after 10 days of germination, or after more than 10 days of germination. In a preferred embodiment, the active barley is processed after 7-8 days of germination. In some embodiments, the active barley is tested for GAA activity and processed when the GAA activity is at a peak level for that barley variety.

In other embodiments of the methods and compositions described herein, the barley is hydrated and allowed to germinate without the use of gibberellic acid. Gibberellic acid treatment synchronizes seed germination, but is not required. Freshly harvested barley does not germinate efficiently due to inhibitors native to the barley seeds that provide a natural dormancy to prevent premature germination of the seed immediately after harvesting. These native inhibitors are destroyed either by aging or by lowering the temperature of the seeds in a manner similar to a winter chill. Usually, storing the barley for about 30 to 90 days is sufficient to impart a good germinating capacity without the use of gibberellic acid. In some embodiments, the barley is processed after 1 day of germination without the use of gibberellic acid, after 2 days of germination without the use of gibberellic acid, after 3 days of germination without the use of gibberellic acid, after 4 days of germination without the use of gibberellic acid, after 5 days of germination without the use of gibberellic acid, after 6 days of germination without the use of gibberellic acid, after 7 days of germination without the use of gibberellic acid, after 8 days of germination without the use of gibberellic acid, after 9 days of germination without the use of gibberellic acid, after 10 days of germination without the use of gibberellic acid, or after more than 10 days of germination without the use of gibberellic acid. In a preferred embodiment, the barley is processed after 7-8 days of germination. In some embodiments, the barley is tested for GAA activity and processed when the GAA activity is at a peak level for that barley variety.

According to this and other aspects of methods and compositions described herein, the barley seeds can be derived from a suitable variety or cultivar such as Morex or Robust. Barley seeds can also be from a variety such as, but not limited to, Nupana, Bomi, Sloop, Carlsberg II, K8, L1, Vlamingh, Stirling, Hamelin, Schooner, Baudin, Gairdner, Buloke, WI3586-1747, WI3416, Flagship, Cowabbie, Franklin, SloopSA, SloopVic, Quasar, VB9104, Grimmett, Cameo*Arupo 31-04, Prior, Schooner, Unicorn, Harrington, Torrens, Galleon, Dhow, Capstan, Fleet, Keel, Maritime, Yarra, Dash, Doolup, Fitzgerald, Molloy, Mundah, Onslow, Skiff, Unicorn, Yagan, Chebec, Hindmarsh, Chariot, Diamant, Koral, Rubin, Bonus, Zenit, Akcent, Forum, Amulet, Toler, Heris, Maresi, Landora, Caruso, Miralix, Wikingett Brise, Caruso, Potter, Pasadena, Annabell, Maud, Extract, Saloon, Prestige, Astoria, Elo, Cork, Extract, or Laura.

According to this and other aspects of the methods and compositions described herein, after germination, active barley can be dried for processing. In some embodiments, the active barley is dried in a commercial dryer. In some embodiments, the active barley is dried to less than 5% moisture content. In some embodiments, the active barley is dried at 4° C., at 5° C., at 6° C., at 7° C., at 8° C., at 9° C., at 10° C., at 11° C., at 12° C., at 13° C., at 14° C., at 15° C., at 16° C., at 17° C., at 18° C., at 19° C., at 20° C., at 21° C., at 22° C., at 23° C., at 24° C., at 25° C., at 26° C., at 27° C., or at 28° C., or any temperature between those indicated.

For larger scale germination and production of active barley, the barley can be steeped in water for about 2 to 3 days at a temperature of about 10° to 25° C., until a moisture content of about 35% to 47% by weight is achieved to promote uniform germination of the barley seeds. The steeping operation is usually carried out in a large cylindrical tank having a conical bottom with means for vigorous aeration and mixing of the steep mixture. The steeped barley is next transferred to the germinating rooms where it can be kept under carefully controlled conditions of moisture, aeration, temperature and time. Such conditions are well known and will generally vary from malthouse to malthouse. When the barley seed germinates to an acceptable level, the seed is dried. Here, the germinated barley seeds are subjected to high air flow and dried at about 10° C. to 25° C.

According to this and other aspects of the methods and compositions described herein, the active barley can be comminuted. In some embodiments, without limitation, the active barley can be dehulled prior to being comminuted. In some embodiments, the active barley can be pulverized or milled. In other embodiments, the milled barley may be a whole grain flour or an ultrafine-milled whole grain flour.

In some embodiments, the bGAA is purified from the GGB. In some embodiments, the bGAA is in a 100-50 kD size fraction. In some embodiments, the bGAA is ~70 kD.

In another embodiment of the methods and compositions described herein, the administering of active barley is carried out orally.

According to this and other aspects of the methods and compositions described herein, the administering of active barley is carried out daily in a single dose or multiple doses. In some embodiments, the administering is carried out daily in a single dose. In some embodiments, the administering is carried out daily in two doses. In some embodiments, the administering is carried out daily in three doses. In some embodiments, the administering is carried out daily in four doses. In some embodiments, the administering is carried out daily in more than four doses.

While the compositions described herein may be administered as the raw active barley form, it is also possible to present them as a pharmaceutical composition. Accordingly, provided herein are pharmaceutical compositions which comprise one or more of certain compounds disclosed herein together with one or more pharmaceutically acceptable excipients or carriers thereof and optionally one or more other therapeutic ingredients. As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. Proper formulation of the pharmaceutical composition is dependent upon the route of administration chosen. Any of the well-known techniques and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Compositions disclosed herein suitable for oral administration may be presented as discrete units such as capsules, cachets or tablets each containing a predetermined amount of the active barley ingredient; as a powder or granules; as a solution or a suspension in an aqueous liquid or a non-aqueous liquid; or as an oil-in-water liquid emulsion or a water-in-oil liquid emulsion. The active barley ingredient may also be presented as a bolus, electuary or paste. As used herein, the term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, hereby incorporated by reference in its entirety.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

According to this and other aspects of the methods and compositions described herein, compositions may be administered at a daily dose of about 0.1 to 10 g/kg of the subject per day. Suitable daily doses for the administering include, without limitation, daily doses of about 0.1 to 0.5 g/kg of the subject per day, about 0.5 to 1 g/kg of the subject per day, about 1 to 3 g/kg of the subject per day, about 2 to 4 g/kg of the subject per day, about 3 to 5 g/kg of the subject per day, about 4 to 6 g/kg of the subject per day, about 5 to 7 g/kg of the subject per day, about 6 to 8 g/kg of the subject per day, about 7 to 9 g/kg of the subject per day, about 8 to 10 g/kg of the subject per day or any value between any of the ranges disclosed above.

The amount of compound or composition administered to a subject will vary depending upon what is being administered, the purpose of the administration, the state of the patient, the manner of administration, and the like. In therapeutic applications, compositions can be administered to a patient already suffering from a disease in an amount sufficient to cure or at least partially arrest the symptoms of the disease and its complications.

For preparing solid compositions such as tablets, the principal active ingredient can be mixed with a pharmaceutical excipient or carrier to form a solid pre-formulation composition containing a homogeneous mixture of a compound of the present application. The tablet pill or capsule of the present application can be an immediate release form. As used herein the term "immediate release" refers to pharmaceutical compositions that release the active ingredient within a short period of time.

The tablets or pills of the present application can be coated or otherwise compounded to provide a dosage form affording the advantage of prolonged action or modified release form, or extended release form. As used herein the term "modified release" refers to pharmaceutical compositions that do not otherwise release the active ingredient immediately. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally include aqueous solutions, suitably flavored syrups, aqueous or oil suspensions, and flavored emulsions with edible oils such as cottonseed oil, sesame oil, coconut oil, peanut oil, soybean oil, or mineral oil as well as elixirs and similar pharmaceutical vehicles.

Another aspect of the present application is directed to a method of replacing acid maltase and/or acid α-glucosidase in a subject. This method involves selecting a subject in need of replacing acid maltase and/or acid α-glucosidase and administering active barley in comminuted form to the selected subject to replace acid maltase and/or acid α-glucosidase in the selected subject.

This aspect of the present application can be carried out with the formulations and modes of administration described above.

Yet another aspect of the present application is directed to a therapeutic composition comprising active germinated barley in comminuted form and an edible pharmaceutically acceptable carrier.

This aspect of the present application can be carried out with the formulations described above.

A further aspect of the present application is directed to a therapeutic system comprising active germinated barley in comminuted form and an enzyme replacement therapeutic.

This aspect of the present application can be carried out with the formulations described above.

EXAMPLES

Example 1

Barley GAA and Development of Ground Germinated Barley

Barley GAA

The sequence for the barley (*Hordeum vulgare*) GAA gene (AGL97, high pI alpha-glucosidase) is GenBank Accession No. AF118226.1, which is hereby incorporated by reference in its entirety. This gene encodes a barley GAA protein of 877 amino acids (GenBank Accession No. AAB02985, which is hereby incorporated by reference in its entirety). In contrast, the *Homo sapiens* GAA gene encodes a larger 952 aa protein (GenBank Accession No. NP_000143, which is hereby incorporated by reference in its entirety). A comparison of the human and barley proteins using NCBI/BLAST/BLASTP suite showed only 39% identity and 55% sequence similarity over a limited portion of the sequence (783 amino acids) between the barley and human GAA proteins.

To induce expression of barley GAA, barley varieties Morex or Robust were surface sterilized by soaking in 3-5% bleach for 5 min., washed with water and placed on paper towels saturated with gibberellic acid ("GA") at 0.05 mg/ml (0.14 mM or 50 ppm) for 1 day at room temperature ("RT"). Paper towels were replaced with fresh water followed by germination for 2-10 days in the dark at RT. Germinated seeds with shoots and roots removed were stored at −20° C.

Figure 1:
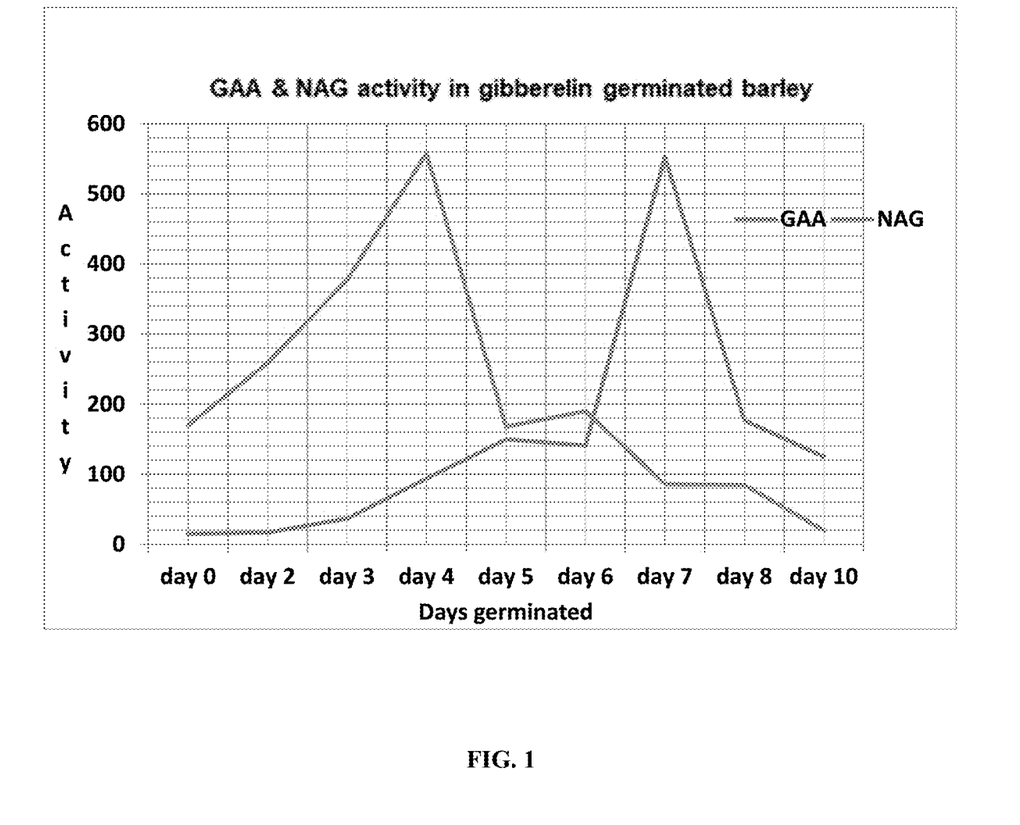
FIG. 1 is a graph showing acid α-glucosidase ("GAA") and neutral α-glucosidase ("NAG") activity in gibberellin germinated barley. Barley GAA ("bGAA") activity peaked at days 7-8 of germination in Morex and Robust barley varieties.

After germination, barley seeds were suspended in 0.01M sodium phosphate buffer (pH 7.5) and homogenized with a pestle followed by centrifugation at 14,000 g for 10 minutes to recover the supernatants. Barley GAA ("bGAA") and neutral α-glucosidase ("NAG") activities were determined using 100 μl of sample and 100 μl of the fluorescent substrate 4-methylumbelliferyl-α-D-glucoside at pH 4.0 for bGAA and pH 7.5 for NAG for 24 hours at 37° C. (FIG. 1) (van Gelder et al., "Enzyme Therapy and Immune Response in Relation to CRIM Status: The Dutch Experience in Classic Infantile Pompe Disease," *J Inherit Metab Dis.* 38:305-314 (2015), which is hereby incorporated by reference in its entirety). Fluorescence was determined in a fluorimeter (excitation-360 nm and emission-460 nm; Sequoia-Turner) (Martiniuk et al., "Correction of Glycogen Storage Disease Type II by Enzyme Replacement With a Recombinant Human Acid Maltase Produced by Over-Expression in a CHO-DHFR (Neg) Cell Line," *Biochem Biophys Res Commun.* 276:917-923 (2000), which is hereby incorporated by reference in its entirety). bGAA was 0.1 μg/g of GGB. GA stimulation and a time-course of expression for bGAA activity from Morex and Robust strains showed a maximum activity of bGAA at days 7-8 (FIG. 1). bGAA also hydrolyzed glycogen similarly to placental human GAA. Un-germinated barley did not show an increase in bGAA.

Ground Germinated Barley

At 8-days after germination, wet barley seeds were dried in a commercial food-dryer, ground, UV sterilized and stored at RT. Processed seeds lost ~75% water weight with no loss in bGAA activity. Thus, 6-wet seeds weighing 0.5 g become 0.15 g of ground germinated barley ("GGB") after drying and grinding.

Figure 2:
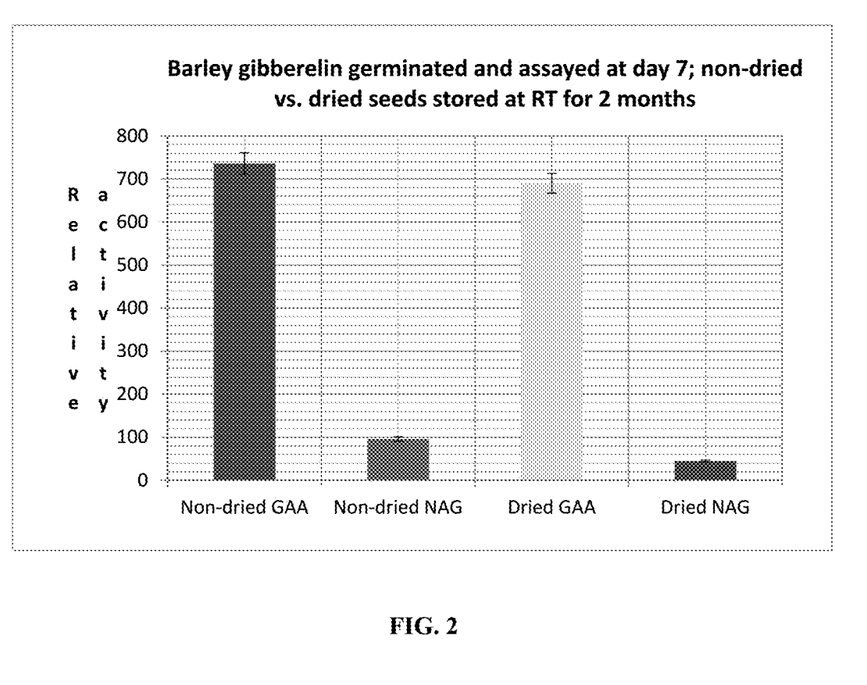
FIG. 2 is a bar graph showing barley germinated with gibberellin and assayed at day 7 of germination in non-dried versus dried seeds that were stored for 2 months at room temperature. Analysis of bGAA and NAG activity in the samples showed that there was no reduction in bGAA activity (mean±SD) due to drying and storage. Thus, bGAA in germinated seeds was stable at room temperature for months.

Dried germinated seeds stored for 2 months at RT had no reduction in bGAA activity (mean±SD) compared to non-dried seeds at 7 days after germination (FIG. 2). This result demonstrated that bGAA in germinated seeds was stable for months. Further testing of ground germinated barley (GGB) stored for 1 year at RT compared to freshly produced GGB showed less than 5% difference in bGAA activity between the two preparations indicating extreme stability of bGAA in GGB.

Ten other grains (corn, millet, rye, wheat, sorghum, buckwheat, quinoa, rice, sunflower and oats) were also tested for GA stimulation over a time-course (up to day 10) for expression of grain specific GAA to compare to the barley Morex or Robust strain profiles for bGAA. Assays for GAA and neutral α-glucosidase (NAG) in lysates from these grains for 10 days of germination demonstrated that these grains did not have any substantial increase in GAA or NAG profiles as compared to the barley Morex and Robust strains. Thus, the bGAA/NAG profile was unique to barley. GAA and NAG activities were determined using the fluorescent substrate 4-methylumbelliferyl-α-D-glucoside (4-MU-Glc) at pH 4.0 for GAA and pH 7.5 for NAG.

Example 2

GAA KO Mouse Model of Glycogen Storage Disease

To address the efficacy of GGB for treatment of glycogen storage disease caused by GAA deficiency, a mouse model for AMD generated by knocking out the GAA gene was used (Raben et al., "Targeted Disruption of the Acid Alpha-Glucosidase Gene in Mice Causes an Illness with Critical Features of Both Infantile and Adult Human Glycogen Storage Disease Type II," *J Biol Chem.* 273:19086-19092 (1998), which is hereby incorporated by reference in its entirety).

The GAA knockout ("KO") mouse lacks GAA activity and recapitulates critical features of the infantile and the adult forms of AMD. This mouse accumulates glycogen in the lysosomes of cardiac and skeletal muscles by 3 weeks while older mice accumulate glycogen in the diaphragm, develop muscle wasting and reduced mobility/strength by 8-9 months. In GAA KO mice treated with rhGAA (20 mg/kg/wk for 5 mo.), skeletal muscle took up minimal enzyme compared to liver and heart. Glycogen reduction was <50% and some fibers showed no glycogen clearance. A dose of 100 mg/kg/wk rhGAA resulted in ~75% glycogen clearance in skeletal muscle (Raben et al., "Enzyme Replacement Therapy in the Mouse Model of Pompe Disease," *Mol Genet Metab.* 80:159-169 (2003), which is hereby incorporated by reference in its entirety).

Neuropathology is prominent in patients with AMD, and GAA KO mice also display temporal neuropathological and behavioral phenotypes (DeRuisseau et al., "Neural Deficits Contribute to Respiratory Insufficiency in Pompe Disease," *PNAS* 106:9419-9424 (2009); Mancal et al., "Pompe's Disease (Diffuse Glycogenosis) with Neuronal Storage," *J Neuropathol Exp Neurol.* 24:85-96 (1965); Sidman et al., "Temporal Neuropathological and Behavioral Phenotype of 6Neo/6Neo Pompe Disease Mice," *J Neuropathol Exp Neurol.* 67:803-818 (2008), each of which is hereby incorporated by reference in their entirety).

In GAA KO mice, excess glycogen accumulates within large neurons of hindbrain, spinal cord, and sensory ganglia by 1-month. Severe degeneration in axon terminals of primary sensory neurons occurs at 3-9 months. GAA KO mice show progressive impairment on Rotarod, wire hanging and foot fault tests (Sidman et al., ibid). These phenotypes allow the assessment of barley GAA and GGB efficacy in treating glycogen storage diseases resulting from mutations in the GAA gene and deficient GAA activity.

Example 3

Evaluation of GGB Lysate in WBC from Human and GAA KO Mice

Figure 3:
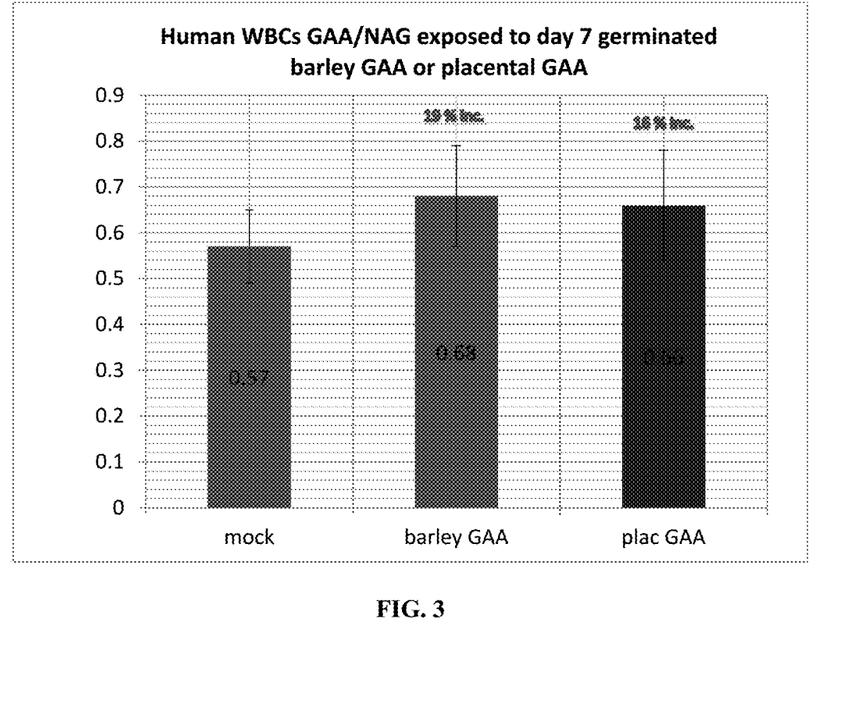
FIG. 3 is a bar graph showing the GAA/NAG ratio after uptake of a crude lysate of day 7 germinated barley GAA by isolated human white blood cells ("WBCs") compared to uptake of placental human GAA as a positive control (mean±SD).
Figure 4:
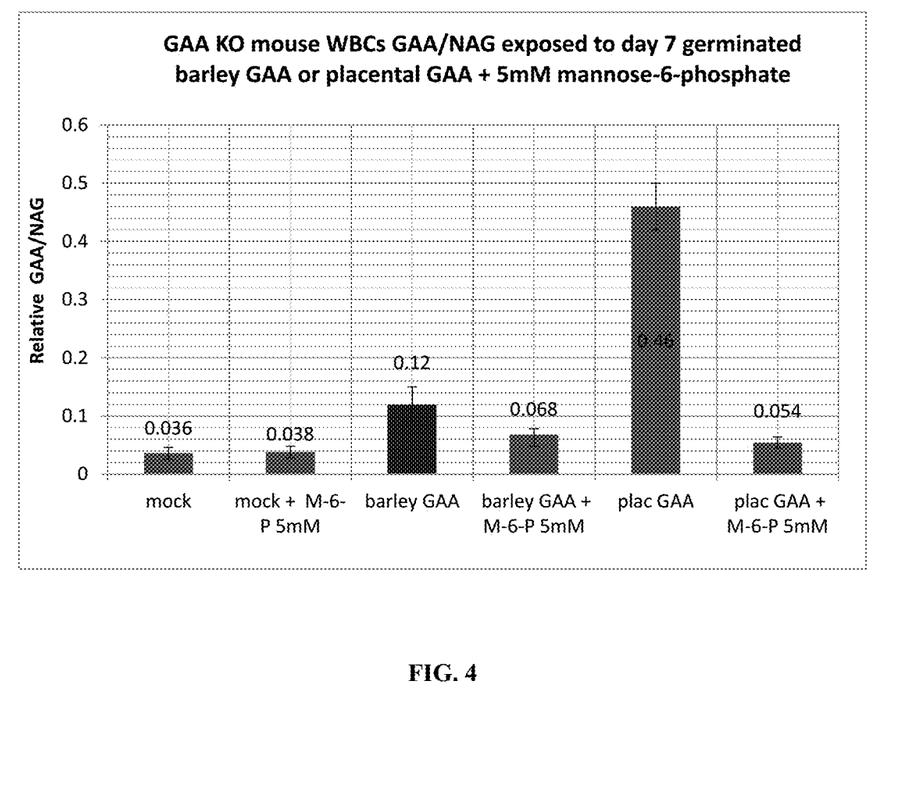
FIG. 4 is a bar graph showing GAA knockout ("KO") mice white blood cells and their GAA/NAG ratio after uptake of day 7 barley GAA or placental human GAA treated with and without 5 mM mannose-6-phosphate, (which blocks uptake by M-6-P receptor). bGAA was taken up by mouse GAA KO WBCs and blocked by mannose-6-phosphate similar to human placental GAA (mean±SD).

Uptake of a crude lysate of 7-8 day GGB by white blood cells ("WBC") from humans and GAA KO mice was tested. Each treatment was performed±5 mM mannose-6 phosphate. Mannose-6 phosphate treatment blocks uptake by the M-6-P receptor (Martiniuk et al., "Further Studies of The Structure of Human Placental Acid Alpha-Glucosidase," *Arch Biochem Biophys* 231:454-460 (1984); Martiniuk et al., "Production of a Functional Human Acid Maltase in Tobacco Seeds: Biochemical Analysis, Uptake by Human GSDII Cells, and in vivo Studies in GAA Knockout Mice," *Appl Biochem Biotechnol* 171:916-926 (2013), each of which is hereby incorporated by reference in their entirety). Human placental GAA (hGAA) was used as a positive control. Anti-coagulate-EDTA was added at 1.5 to 2.0 mg/ml of whole blood. 0.15 ml of human and mouse KO blood was used and a 14×RBC lysing solution ($NH_4Cl$ (ammonium chloride)—8.02 g; $NaHCO_3$ (sodium bicarbonate)—0.84 g; EDTA (disodium)—0.37 g to 100 ml with water) was added in a 1.5 ml microfuge tube, inverted for 10 minutes at RT until the liquid was clear red followed by spinning for 1 minute in a microfuge. The supernatant was decanted, cells were washed with phosphate buffered saline (PBS) and re-suspend in 2.4 ml complete DMEM-10% FBS (Life Technologies). Cells were divided into 6 microfuge tubes, 70 μl of lysate of germinated barley at day 7 or 70 μl placental hGAA or 70 μl PBS was added and placed at 37°

C. for 18 hrs. In one set, mannose-6-phosphate (5 mM) was added to block uptake. Lysed cells were assayed for GAA and NAG. Human WBCs exposed to day 7 germinated barley GAA or placental hGAA had higher ratios of GAA/NAG compared to mock treated cells (FIG. 3). bGAA was also taken up by mouse GAA KO WBCs and uptake was blocked by mannose-6-phosphate similar to human placental hGAA (mean±SD) (FIG. 4). These experiments indicated that human and mouse WBCs could take up bGAA.

Example 4

Response of GAA KO Mice to bGAA and GGB

Figure 5:
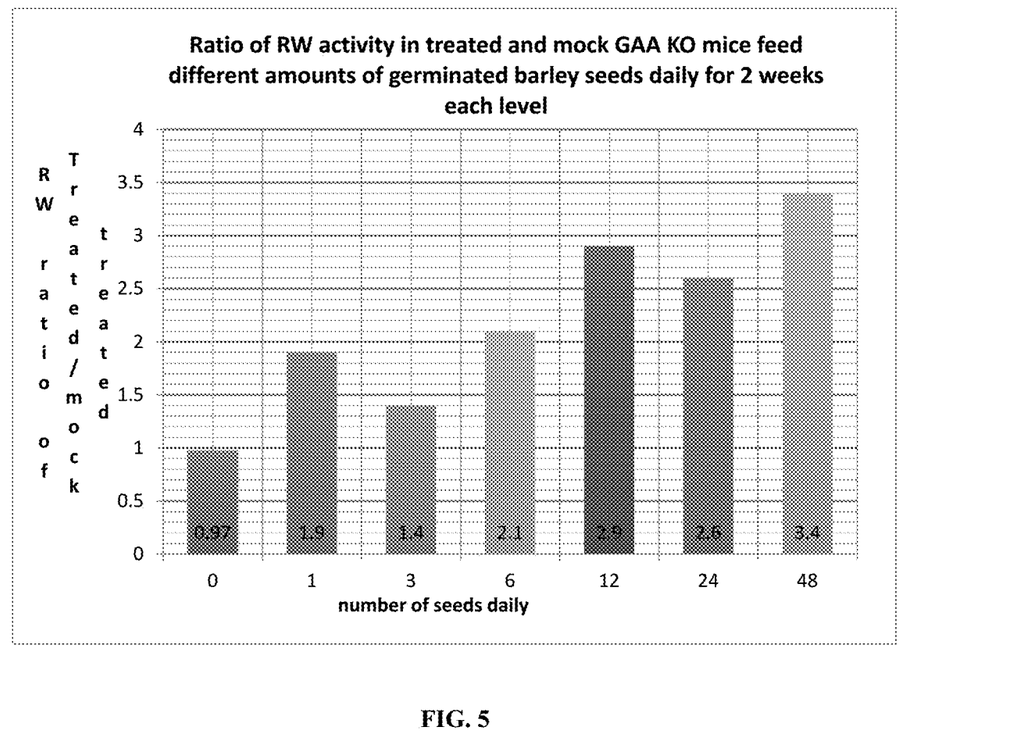
FIG. 5 is a bar graph showing the ratio of running wheel ("RW") activity in treated and mock treated GAA KO mice fed different amounts of germinated barley seeds daily for 2 weeks at each level. Feeding GAA KO mice germinated barley seeds reversed hind-limb muscle weakness as assessed by increased RW activity in a dose dependent manner. GAA KO mice treated daily with un-germinated seeds showed no increase in RW activity.

GAA KO mice (~6 months old) were fed daily with germinated (7-day germination) active barley seeds containing bGAA in amounts of either 0, 1, 3, 6, 12, 24 or 48 seeds for two weeks at each level. Upon consuming bGAA, GAA KO mice showed a reversal in hind-limb muscle weakness as assessed by increased running wheel (RW) activity that was dose dependent (FIG. 5). GAA KO mice treated daily with un-germinated seeds showed no increase in RW activity.

GGB was prepared by processing 8-day germinated wet barley seeds by drying in a commercial food-dryer, grinding them, UV sterilizing the material and storing at RT. GAA KO mice were treated daily with GGB on peanut butter at 0.2 g/mouse for 3 weeks followed by feeding them GGB at 0.3 g/mouse for 3 weeks and then GGB at 0.4 g/mouse for 3 weeks. Control mice were fed peanut butter only. After 3 weeks of feeding at each dose, mice were evaluated for motor activity by running wheel (RW); fore-limb muscle strength by grip-strength meter (GSM), motor coordination/balance with a Rotarod, open-field mobility by 5-min video, CBC (complete blood count) differentials and spontaneous learning with a T-maze (Table 1). The * indicates p=<0.05 when compared to pre-treatment data by T-test (1-tail, 2-equal variance).

pared to only 43 (±38) for the GAA KO mice. The GGB fed GAA KO mice had significantly increased times, staying on the rotating rod for up to 103 (±79) seconds.

The T-maze test to evaluate spontaneous learning showed an increase in the % correct alternation for GGB fed GAA KO mice compared to control GAA KO mice. Thus, statistically significant improvements from pre-treated GAA KO mice for RW, GSM, Rotarod and T-maze were observed for all three doses of GGB administration. CBC differentials of treated GAA KO animals were identical to pre-treatment and treated GAA KO plus WT mice.

Spontaneous alternation is used to assess the cognitive ability of rodents to choose one of the 2 goal arms of the T-maze (Deacon and Rawlins, "T-Maze Alternation in the Rodent," *Nature Protocols* 2006; 1:7-12, hereby incorporated by reference in its entirety). The advantage of a free choice procedure is that hippocampal or lesioned animals often develop a side preference and scores below 50%. Controls generally achieve at least 60-80% correct alternation. Spontaneous alternative learning for cognitive ability was assessed in the T-maze in both male and female GAA KO mice and WT mice from 2-9 mo of age. It was found that deficiency in spontaneous learning appeared by 2-3 months in male and 3-4 months in female GAA KO mice. All conditions were significant (p<0.05).

IL-6 baseline for WT and GAA KO mice in serum with the PeproTech's pro-inflammatory cytokine IL6 ELISA was measured every 2 weeks for 3 months. The IL-6 levels for all were below detection of the lowest standard of 16 pg/ml.

These experiments revealed that GAA from barley in the form of GGB significantly improved motor and cognitive neurological functions as assessed by multiple different tests in GAA KO mice in a dose dependent manner. Running wheel times, grip strength meter, Rotarod performance tests, T-maze and spontaneous alternation tests were all significantly improved compared to GAA KO mice that did not receive GGB.

TABLE 1

Effect of GGB on GAA KO Mice

| Treatment Mean ± SD | RW rev/12 hrs | GSM lbs at release | Rotarod Time (sec) | T-maze % correct alternation | Open-field mobility cm/min ± SD | CBC diff. |
|---|---|---|---|---|---|---|
| GAA KO M/F n = 4 | 795 ± 50 | 0.1070 ± 0.32 | 43 ± 38 | 32 ± 10 | 174 ± 108 | Nl. |
| GAA KO Tx 0.2 g/mo | 2694 ± 1409* | 0.304 ± 0.13* | 84 ± 67* | ND | 242 ± 74 | Nl. |
| GAA KO Tx 0.3 g/mo | 5893 ± 3445* | 0.285 ± 0.13* | 77 ± 41* | 69 ± 6* | 158 ± 106 | Nl. |
| GAA KO Tx 0.4 g/mo | 3427 ± 1526* | 0.308 ± 0.19* | 103 ± 79* | ND | 150 ± 84 | Nl. |
| WT M/F n = 8 | 4912 ± 2316 | 0.627 ± 0.265 | 245 ± 98 | 61 ± 10 | 334 ± 96 | Nl. |

Compared to WT mice having running wheel (RW) times of 4912 (±2316) revolutions/12 hours (rev/12 hrs), the GAA KO mice only had an average of 795 (±50) rev/12 hrs RW times (6 fold fewer revolutions). However, the GAA KO mice fed GGB had significantly increased RW motor activity than GAA KO mice with an average RW time up to 5893 (±2316) rev/12 hrs RW times increased (3.4 to 7.4 fold more revolutions) in GAA KO mice fed GGB compared to GAA KO mice not fed GGB.

The grip-strength meter (GSM) of GAA KO mice was only 0.107 (±0.32) compared to 0.627 (±0.265) for WT mice. In contrast, the GGB fed GAA KO mice had significantly increased GSM compared to GAA KO mice of up to 0.308 (±0.19).

In the Rotarod performance test, the WT mice stayed on the rotating rod for an average of 245 (±98) seconds com- These results were unexpected given that the barley GAA protein has only approximately 39% sequence identity and 55% sequence similarity over a limited portion of the protein compared to the human GAA protein. Despite the low sequence similarity, the barley GAA enzyme was shown to be taken up by both human and murine white blood cells in a similar fashion as human recombinant GAA. Furthermore, the oral delivery of barley GAA was shown to be efficacious in improving multiple indices of skeletal muscle and cognitive neurological function that were affected by the lysosomal storage disorder caused by GAA deficiency.

GGB has many advantages over the current treatments for GAA deficiency. The cost of producing GGB is very low compared to the costs of producing recombinant GAA, and GGB is extremely stable at room temperature. GGB is easily administered, and does not require a visit to a physician's office or clinic, or intravenous infusion as required by the current treatment. Furthermore, GGB showed a reduced or absent immunological reaction, and an ability to reverse neurological problems.

Example 5

Purification and Further Analysis of bGAA

GGB lysate was prepared from barley seeds that were homogenized in 1.2 times volume of 0.001 M sodium phosphate, pH 7.5 in a blender and stored at 4° C. overnight. The homogenate was filtered through 2 layers of fine cheesecloth at 4° C., followed by passing through a 200 mesh nylon membrane and stored at 4° C.

Lysates of GGB were analyzed for biologic contaminates using R-Cards from Roth Bioscience LLC (Goshen, IN, rothbioscience.com) for *Salmonella* species, *E. coli*, yeast/mold and *Listeria* species. Briefly, for specific R-cards, the top plate was lifted, 1 ml of sample was placed on the center of the card, then the card was slowly re-covered with the top plate. After standing for 1 minute so that the sample was evenly spread, the R-cards were incubated at 37° C. overnight for all organisms except yeast which was placed at 25° C. for 24-72 hours. Sensitivity was one organism/ml. No biologic contaminates were found in the lysate from GGB.

Figure 6:
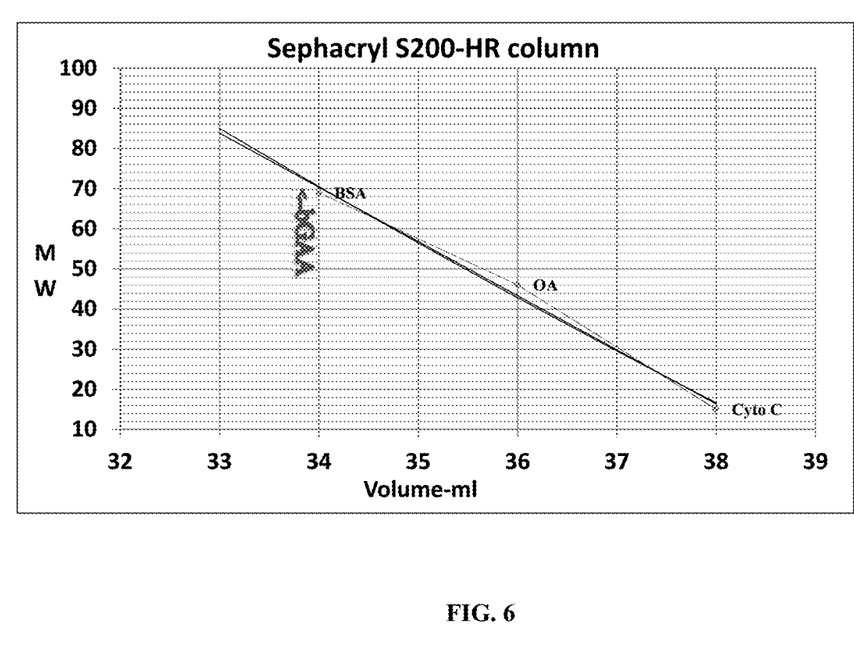
FIG. 6 is a line graph showing determination of bGAA molecular weight by chromatography on Sephacryl S200 HR with an extract of GGB. Peak bGAA activity eluted at a MW of ~70 kD. The bGAA was partially purified by size inclusion between Amicon YM 50 kD and 100 kD membranes. Standards used for size determination were bovine serum albumin ("BSA") (69 kD), ovalbumin ("OA") (48 kD), and cytochrome C ("Cyto-C") (14 kD).

Partial purification of bGAA from the GGB lysate was performed by size exclusion using Amicon YM 50 kD and 100 kD membranes (MilliporeSigma, Burlington Mass.). Chromatography of bGAA on Sephacryl S200 HR showed that bGAA peak activity eluted at a molecular weight of ~70 kD (FIG. 6). Standards used for size determination were bovine serum albumin (BSA) (69 kD), ovalbumin (OA) (48 kD), and cytochrome C (Cyto-C) (14 kD).

Figure 7:
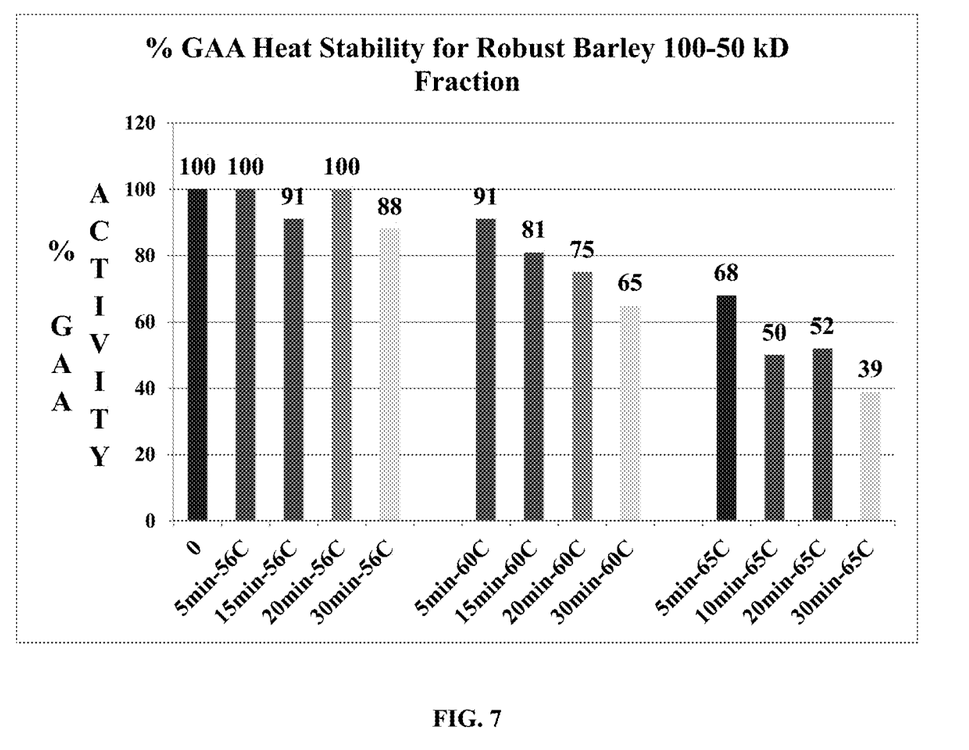
FIG. 7 is a bar graph showing the heat stability of bGAA. bGAA was treated at three temperatures (56° C., 60° C., or 65° C.) for 5, 10, 15, 20, or 30 minutes and assayed for GAA activity. Activity is shown compared to untreated bGAA (100% activity).

Heat stability of purified bGAA was determined by incubation of 25 µl of the 100-50 kD bGAA fraction for various times over three temperatures (FIG. 7). The temperatures tested were either 56° C., 60° C., or 65° C. bGAA was tested for 5, 10, 15, 20 or 30 minutes at each temperature and assayed for GAA activity. These data show that bGAA is extremely heat stable at 56° C. for up to 30 minutes. Stability at 60° C. and 65° C. declined rapidly over the 30 minute treatment (FIG. 7).

Figure 8:
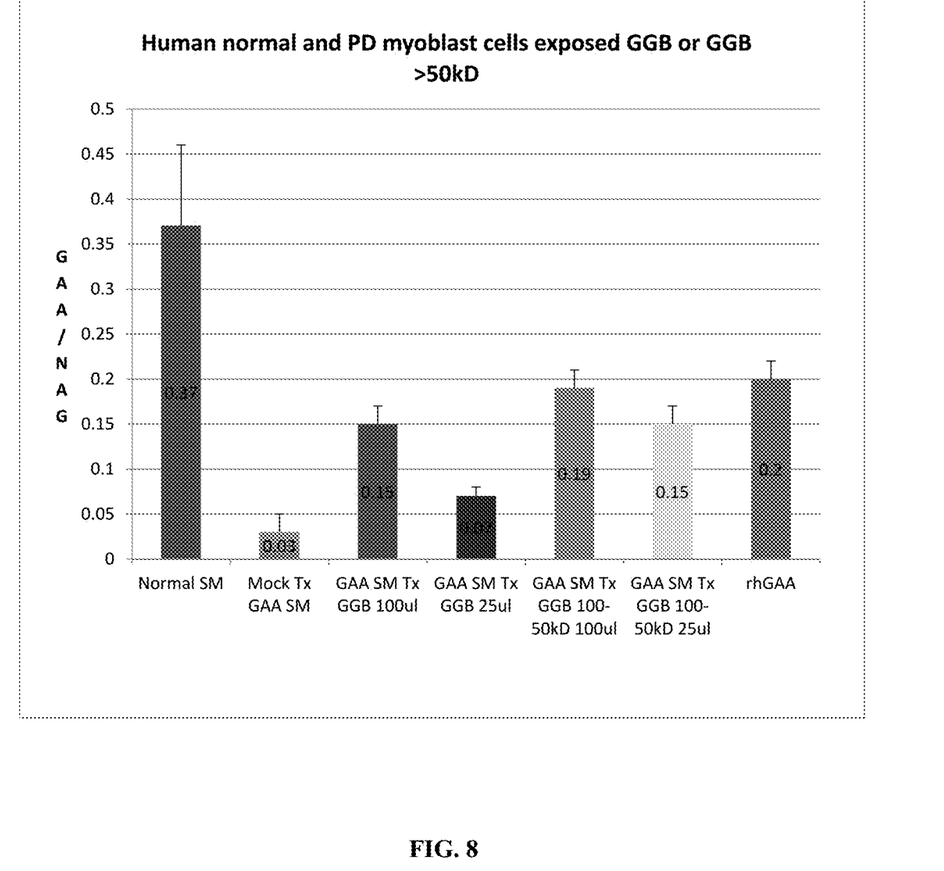
FIG. 8 is a bar graph showing the uptake of GGB or 100-50 kD fraction of bGAA in human skeletal muscle and PD lymphoid cell lines.

A human skeletal PD muscle cell line (homozygous for the IVS1 c.-32-13t>g) was plated at 0.3-0.4×10⁶ in a 6 well plate with PromoCell skeletal muscle growth media (PromoCell, Heidelberg, Germany). Cells were exposed equivalent amounts of GGB or the purified 100-50 kD bGAA fraction for 48 hours. Cells were harvested after various hours of exposure, washed with PBS, lysed by addition of 0.5 ml of 0.01 M sodium phosphate pH 7.5, frozen and thawed three times, spun for 5 minutes to clarify, and assayed for human GAA and NAG. Controls included normal skeletal muscle cells, mock treated human skeletal PD muscle cells, and PD muscle cells treated with equivalent amounts of an rhGAA (R&D Systems #8329-GH-025, Minneapolis, MN). As shown in FIG. 8, both GGB and the 100-50 kD purified bGAA fraction increased GAA to 19-51% of normal (mean±SD).

Figure 9:
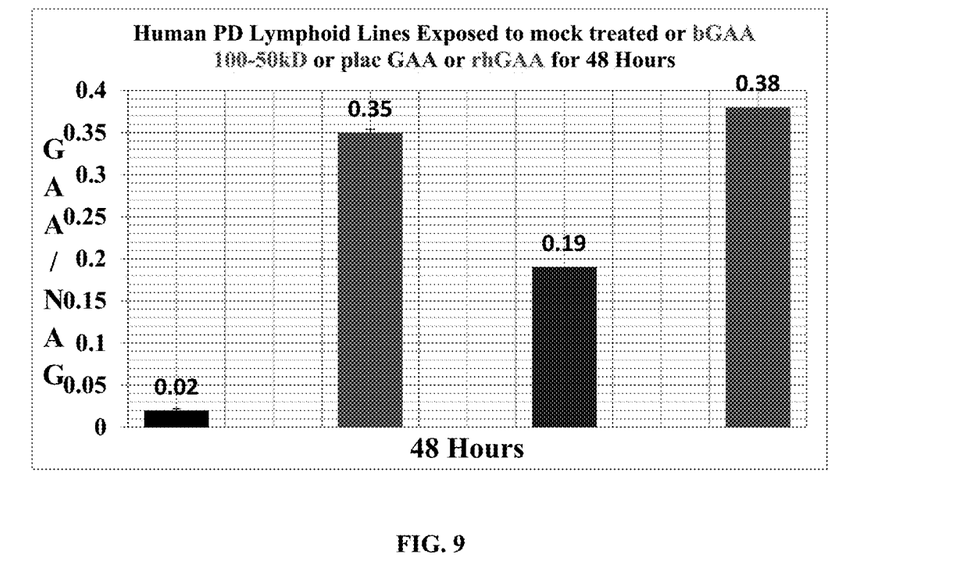
FIG. 9 is a bar graph showing human PD lymphoid lines exposed to mock treatment, the bGAA 100-50 kD fraction, placental GAA, or rhGAA for 48 hours (treatments shown from left to right, respectively).

Human lymphoid (GM6314, GM13793, GM14450) cell lines from infantile or adult PD subjects were maintained in 15% fetal bovine serum, RPMI 1640 supplemented with glutamine, penicillin and streptomycin at 37° C. and 5% $CO_2$. Cells were plated at 0.3-0.4×10⁶ per 6-well in 1.5 ml media for 24 hours before addition of varying amounts of bGAA (100-50 kD fraction), placental GAA, or rhGAA for 48 hours and assayed (FIG. 9). At 48 hours, equivalent concentrations showed similar uptake and increases in GAA (mean±SEM).

Although preferred embodiments have been depicted and described in detail herein, it will be apparent to those skilled in the relevant art that various modifications, additions, substitutions, and the like can be made without departing from the spirit of the present application and these are therefore considered to be within the scope of the present application.

What is claimed:

1. A method of treating a lysosomal storage disease resulting from a deficiency of acid maltase and/or acid α-glucosidase, said method comprising:
    selecting a subject having a lysosomal storage disease resulting from a deficiency of acid maltase and/or acid α-glucosidase, and
    administering ground germinated barley (GGB) to the selected subject to treat the lysosomal storage disease;
    wherein the GBB possesses barley acid α-glucosidase (bGAA) enzymatic activity; and
    wherein the lysosomal storage disease is selected from the group consisting of a glycogen storage disease type II, acid maltase deficiency, Pompe's disease, and combinations thereof.

2. The method of claim 1, wherein the lysosomal storage disease is glycogen storage disease type II.

3. The method of claim 2, wherein the lysosomal storage disease is infantile glycogen storage disease type II.

4. The method of claim 2, wherein the lysosomal storage disease is juvenile glycogen storage disease type II.

5. The method of claim 2, wherein the lysosomal storage disease is adult-onset glycogen storage disease type II.

6. The method of claim 1, wherein said method is carried out in conjunction with enzyme replacement therapy.

7. The method of claim 1, wherein said method is carried out in conjunction with alglucosidase alfa treatment.

8. The method of claim 7, wherein the alglucosidase alfa treatment is carried out intravenously.

9. The method of claim 1, wherein said administering is carried out orally.

10. The method of claim 1, wherein said administering is carried out daily in a single dose or multiple doses of GGB.

11. The method of claim 1, wherein said administering is carried in daily doses of 1 to 3 g/kg of the selected subject.

* * * * *

UNITED STATES PATENT AND TRADEMARK OFFICE
CERTIFICATE OF CORRECTION

| | |
|---|---|
| PATENT NO. | : 11,839,641 B2 |
| APPLICATION NO. | : 17/404680 |
| DATED | : December 12, 2023 |
| INVENTOR(S) | : Martiniuk et al. |

It is certified that error appears in the above-identified patent and that said Letters Patent is hereby corrected as shown below:

On the Title Page

Item (72)
Please add inventor: Kam-Meng Mary Tchou-Wong, New York, NY (US)

Signed and Sealed this
First Day of October, 2024

Katherine Kelly Vidal
*Director of the United States Patent and Trademark Office*